United States Patent [19]
Chatterjee

[11] Patent Number: 5,919,687
[45] Date of Patent: Jul. 6, 1999

[54] RECOMBINANT N-SMASES AND NUCLEIC ACIDS ENCODING SAME

[75] Inventor: Subroto Chatterjee, Columbia, Md.

[73] Assignee: John Hopkins University, Baltimore, Md.

[21] Appl. No.: 08/774,104

[22] Filed: Dec. 24, 1996

[51] Int. Cl.$^6$ .............. C12N 9/22; C12N 15/00; C12N 1/20; C07H 21/04
[52] U.S. Cl. ............ 435/199; 435/6; 435/320.1; 435/252.3; 435/254.11; 435/325; 536/23.2; 536/23.4; 536/24.3
[58] Field of Search ............... 435/6, 198, 199, 435/252.3, 254.11, 320.1, 325; 536/23.2, 24.3

[56] References Cited

U.S. PATENT DOCUMENTS 5,451,518  9/1995  Kolesnick ............... 435/194

FOREIGN PATENT DOCUMENTS 0 520 843 A2  12/1992  European Pat. Off. .

OTHER PUBLICATIONS

Ida et al. (1993) Cloning of a Human Acid Sphingomyelinase cDNA with a New Mutation That Renders the Enzyme Inactive. J. Biochem. 114:15–20.
Liu et al. (1997) Sphingomyelinases in Cell Regulation. Seminars in Cell and Developmental Biology 8: 311–322.
Quintern et al. (1989) Isolation of cDNA Clones Encoding Human Acid Sphingomyelinase: Occurrence of Alternately Processed Transcripts. EMBO J. 8(9): 2469–2473.
Genexpress, H.sapiens partial cDNA sequence; clone 48F08; strand (–), single read, EST–STS Database Accession No. Z13441, submitted Jun. 25, 1992, release date Jun. 4, 1993.
P. Peraldi et al., *The American Society for Biochemistry and Molecular Biology, Inc.*, 271:13018–13022 (1996).
A. Allessenko et al., *Molecular and Cellular Biochemistry*, 143:169–174 (1995).
T. Taki et al., *Analytical Biochemistry*, 224:490–493 (1995).
H. Oral et al., *Circulation*, 94(8), Abstract No. 2377 (1996).
S. Chatterjee, *The Journal of Biological Chemistry*, 269(2):879–882 (1994).
S. Chatterjee et al., *The Journal of Biological Chemistry*, 264(21):12554–12561 (1989).
S. Chatterjee, *The Journal of Biological Chemistry*, 268(5):3401–3406 (1993).
P. Ghosh et al., *The Journal of Biological Chemistry*, 262(26):12550–12556 (1987).
S. Chatterjee, *Advance in Lipid Research*, 26:25–48 (1993).

*Primary Examiner*—Lisa Hobbs
*Attorney, Agent, or Firm*—Peter F. Corless; Cara Z. Lowen; Dike, Bronstein, Roberts & Cushman, LLP

[57] ABSTRACT

Isolated nucleic acids are provided that encode human neutral sphingomyelinase (N-SMase) and N-SMase fragments and derivatives capable of hybridizing to such N-SMase-encoding nucleic acids. The invention also includes isolated recombinant human neutral sphingomyelinase (N-SMase) and N-SMase fragments and derivatives are also provided. Novel assays are also provided to identify compounds useful in the diagnosis or treatment of human neutral sphingomyelinase related disorders.

16 Claims, 8 Drawing Sheets

```
ATGATGACATATCACGAAACGGCGCGTTGGCTCAAAGCGACTTACAGCA
ACTCTATGCGGCACTTGAAACAACTGAATTTGGCGCTTA
CTTTGCGACACCCGCTGATGATACTTTACGTTTTGGCATTGGGCAATCG
CTACGGCAAAAACGGCTCAGGCATTACAAGGTGCGGTTGTTTTGGTGCG
CAGTCATTTGATGAACAAGAGTACCCGCAGTCTGAATTGATGGCGGGTTT
TTGGTTTGTCCCGAAGTGATGGTGACCATGCGGCAGATAAAATCACGT
TCGGATCAGATACCGTATCTGATTTTACGACGTGGCTGGCGCAGTTCGTG
CCAAAACAGCCAAATACGGTGACCACTAGTCATGTGACAGATGAAGTGGA
TTGGATCGAACGGACAGAGAATTTGATGATACCTTAGCCATCGATCAAA
CCTTAGCCAAGTCGTTTTGGTCGGCAACAGACCCTGCAGTTATCCGAC
ACGTTACGACTGGCACAAATTATTCGTGCGTTAGCTGAGCAGGCGAATAC
GTATCATGTGGTTTTAAAGCGACATGATGAATTGTTTATTTCAGCAACAC
CGGAACGGTTAGTGGCTATGTCAGGTGGTCAGATCGCTACGGCGGCGGTC
GCTGGGACAAGCCGGCGCGGGACGGATGGCGCGGATATCGCGTTAGG
CGAAGCGTTGTTAGCCAGTCAGAAAAACCGCATTGAACATGAACATGTCG
TGGCAAGTATCACGACACGCTTGCAAGACGTGACGACGTCGCTAAAGGTG
CCGGCCATGCCAAGTTACTCAAAAATAAGCACATTAAGTGTGACCGCGATTGTTG
ACCAATTACAGGGGACATTGCGGCACACTGGGTGGCGTCCCACGTGAAGCGGCC
ACCGCTTGCATCCAACACCAGCACTGGGTGGCGTCCCACGTGAAGCGGCC
CTGTATTACATTGCGACCCATGAGAAGACACCTCGTGGCTTGTTTGCAGG
TCCTATTGCTATTTACCGCAGATAATAGTGGGGAATTTGTGGTTGGCA
TCCGTTCCATGTATGTGAATCAAACGCAGCGAGCAACTTATTTGCT
GGTGCCGGGATTGTGGCTGACTCCGATGCGCAACAAGAATATGAAGAAAC
TGGGTTGAAATTTGAACCCATGCGGCAATTGTTAAAGGACTACAATCATG
TCGAATGA
```

FIG. 1

```
  1 MMTYHETRALAQSDLQQLYAALETTEFGAYFATPA
 36 DDTLRFGIGAIATAKTAQALQGAVFGAQSFDEQEY
 71 PQSELMAGFWFVPEVMVTIAADKITFGSDTVSDFT
106 TWLAQFVPKQPNTVTTSHVTDEVDWIERTENLIDT
141 LAIDQTLAKVVFGRQQTLQLSDTLRLAQIIRALAE
176 QANTYHVVLKRHDELFISATPERLVAMSGGQIATA
211 AVAGTSRRGTDGADDIALGEALLASQKNRIEHQYV
246 VASITTRLQDVTTSLKVPAMPSLLKNKQVQHLYTP
281 ITGDIAAHLSVTAIVDRLHPTPALGGVPREAALYY
316 IATHEKTPRGLFAGPIGYFTADNSGEFVVGIRSMY
351 VNQTQRRATLFAGAGIVADSDAQQEYEETGLKFEP
385 MRQLLKDYNHVE
```

FIG. 2

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 1197 base pairs
        (B) TYPE: nucleic acid
        (C) STRANDEDNESS: single
        (D) TOPOLOGY: linear (ii) MOLECULE TYPE: cDNA -continued (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

```
ATGATGACAT ATCACGAAAC GCGCGCGTTG GCTCAAAGCG ACTTACAGCA ACTCTATGCG      60
GCACTTGAAA CAACTGAATT TGGCGCTTAC TTTGCGACAC CCGCTGATGA TACTTTACGT     120
TTTGGCATTG GCGCAATCGC TACGGCAAAA ACGGCTCAGG CATTACAAGG TGCGGTTGTT     180
TTTGGTGCGC AGTCATTTGA TGAACAAGAG TACCCGCAGT CTGAATTGAT GGCGGGTTTT     240
TGGTTTGTCC CCGAAGTGAT GGTGACCATC GCGGCAGATA AAATCACGTT CGGATCAGAT     300
ACCGTATCTG ATTTTACGAC GTGGCTGGCG CAGTTCGTGC CAAAACAGCC AAATACGGTG     360
ACCACTAGTC ATGTGACAGA TGAAGTGGAT TGGATCGAAC GGACAGAGAA TTTGATTGAT     420
ACCTTAGCCA TCGATCAAAC CTTAGCCAAA GTCGTTTTTG GTCGGCAACA GACCCTGCAG     480
TTATCCGACA CGTTACGACT GGCACAAATT ATTCGTGCGT TAGCTGAGCA GGCGAATACG     540
TATCATGTGG TTTTAAAGCG ACATGATGAA TTGTTTATTT CAGCAACACC GGAACGGTTA     600
GTGGCTATGT CAGGTGGTCA GATCGCTACG GCGGCGGTCG CTGGGACAAG CCGGCGCGGG     660
ACGGATGGCG CTGACGATAT CGCGTTAGGC GAAGCGTTGT TAGCCAGTCA GAAAAACCGC     720
ATTGAACATC AATATGTCGT GGCAAGTATC ACGACACGCT TGCAAGACGT GACGACGTCG     780
CTAAAGGTGC CGGCCATGCC AAGTTTACTC AAAAATAAGC AAGTTCAGCA TTTGTACACA     840
CCAATTACAG GGGACATTGC GGCACATTTA AGTGTGACCG CGATTGTTGA CCGCTTGCAT     900
CCAACACCAG CACTGGGTGG CGTCCCACGT GAAGCGGCCC TGTATTACAT TGCGACCCAT     960
GAGAAGACAC CTCGTGGCTT GTTTGCAGGT CCTATTGGCT ATTTTACCGC AGATAATAGT    1020
GGGGAATTTG TGGTTGGCAT CCGTTCCATG TATGTGAATC AAACGCAGCG ACGAGCAACT    1080
TTATTTGCTG GTGCCGGGAT TGTGGCTGAC TCCGATGCGC AACAAGAATA TGAAGAAACT    1140
GGGTTGAAAT TTGAACCCAT GCGGCAATTG TTAAAGGACT ACAATCATGT CGAATGA       1197
```

(2) INFORMATION FOR SEQ ID NO:2:

(i) SEQUENCE CHARACTERISTICS:
(A) LENGTH: 397 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:2:

```
Met Met Thr Tyr His Glu Thr Arg Ala Leu Ala Gln Ser Asp Leu Gln
 1               5                  10                  15

Gln Leu Tyr Ala Ala Leu Glu Thr Thr Glu Phe Gly Ala Tyr Phe Ala
                 20                  25                  30

Thr Pro Ala Asp Asp Thr Leu Arg Phe Gly Ile Gly Ala Ile Ala Thr
             35                  40                  45
```

```
Ala Lys Thr Ala Gln Ala Leu Gln Gly Ala Val Phe Gly Ala Gln Ser
 50                  55                  60

Phe Asp Glu Gln Glu Tyr Pro Gln Ser Glu Leu Met Ala Gly Phe Trp
 65                  70                  75                  80

Phe Val Pro Glu Val Met Val Thr Ile Ala Ala Asp Lys Ile Thr Phe
                 85                  90                  95

Gly Ser Asp Thr Val Ser Asp Phe Thr Thr Trp Leu Ala Gln Phe Val
                100                 105                 110

Pro Lys Gln Pro Asn Thr Val Thr Thr Ser His Val Thr Asp Glu Val
                115                 120                 125

Asp Trp Ile Glu Arg Thr Glu Asn Leu Ile Asp Thr Leu Ala Ile Asp
130                 135                 140

Gln Thr Leu Ala Lys Val Val Phe Gly Arg Gln Gln Thr Leu Gln Leu
145                 150                 155                 160

Ser Asp Thr Leu Arg Leu Ala Gln Ile Ile Arg Ala Leu Ala Glu Gln
                165                 170                 175

Ala Asn Thr Tyr His Val Val Leu Lys Arg His Asp Glu Leu Phe Ile
                180                 185                 190

Ser Ala Thr Pro Glu Arg Leu Val Ala Met Ser Gly Gly Gln Ile Ala
                195                 200                 205

Thr Ala Val Ala Gly Thr Ser Arg Arg Gly Thr Asp Gly Ala Asp
210                 215                 220

Asp Ile Ala Leu Gly Glu Ala Leu Leu Ala Ser Gln Lys Asn Arg Ile
225                 230                 235                 240

Glu His Gln Tyr Val Val Ala Ser Ile Thr Thr Arg Leu Gln Asp Val
                245                 250                 255

Thr Thr Ser Leu Lys Val Pro Ala Met Pro Ser Leu Leu Lys Asn Lys
                260                 265                 270

Gln Val Gln His Leu Tyr Thr Pro Ile Thr Gly Asp Ile Ala Ala His
                275                 280                 285

Leu Ser Val Thr Ala Ile Val Asp Arg Leu His Pro Thr Pro Ala Leu
290                 295                 300

Gly Gly Val Pro Arg Glu Ala Ala Leu Tyr Tyr Ile Ala Thr His Glu
305                 310                 315                 320

Lys Thr Pro Arg Gly Leu Phe Ala Gly Pro Ile Gly Tyr Phe Thr Ala
                325                 330                 335

Asp Asn Ser Gly Glu Phe Val Val Gly Ile Arg Ser Met Tyr Val Asn
                340                 345                 350

Gln Thr Gln Arg Arg Ala Thr Leu Phe Ala Gly Ala Gly Ile Val Ala
                355                 360                 365

Asp Ser Asp Ala Gln Gln Glu Tyr Glu Glu Thr Gly Leu Lys Phe Glu
                370                 375                 380

Pro Met Arg Gln Leu Leu Lys Asp Tyr Asn His Val Glu
385                 390                 395
```

(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:3:

Thr Ser Leu Lys Val Pro Ala
1               5

(2) INFORMATION FOR SEQ ID NO:4:

(i) SEQUENCE CHARACTERISTICS:
                (A) LENGTH: 7 amino acids
                (B) TYPE: amino acid
                (C) STRANDEDNESS: single
                (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:4:

Arg Ser Ile Thr Val Arg Val
1               5

(2) INFORMATION FOR SEQ ID NO:5:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

TTGCGGCACT ATTAGGTG                                                    18

(2) INFORMATION FOR SEQ ID NO:6:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

CGCCAATGCC AAAACGTA                                                    18

(2) INFORMATION FOR SEQ ID NO:7:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

GATCCATGAT GACATATCAC GAAACGCGCG TTTCGTGATA TGTCATCATG      50

RECOMBINANT N-SMASES AND NUCLEIC ACIDS ENCODING SAME

BACKGROUND OF THE INVENTION

1. Field of the Invention

The present invention relates to human neutral sphingomyelinases (N-SMases), including recombinant N-SMases and fragments and derivatives thereof and isolated nucleic acids encoding N-SMases and fragments and derivatives. In preferred aspects, assays for identifying compounds that can modulate N-SMase related activity are provided, particularly assays to identify a pharmacological agent useful in the diagnosis or treatment of disorders associated with human neutral sphingomyelinases.

2. Background

Sphingomyelinases type-C (E.C. 3.1.4.12) are a group of phospholipases that catalyze the hydrolytic cleavage of sphingomyelin via the following reaction (1).

Sphingomyelin→Ceramide+Phosphocholine  (1)

Native N-SMase purified from human urine and cultured human kidney proximal tubular cell membranes has an apparent molecular weight of 92 kDa, neutral pH optima, is heat unstable and is localized on the surface of various cells. S. Chatteijee, *Adv. Lipid Res.*, 26:25–48 (1993); S. Chatterjee et al., *J. Biol. Chem.*, 264:12,534–12,561 (1989); and S. Chatterjee et al., *Methods in Enzymology, Phospholipase*, 197:540–547 (1991). N-SMase action has been shown to mediate signal transduction of vitamin $D_3$, tumor necrosis factor-α (TNF-α), interferon-gamma and nerve growth factor (Y. Hannun, *J. Biol. Chem.*, 269:3,125–3,128 (1994); S. Chatterjee, *J. Biol. Chem.*, 268:3,401–3,406 (1993); and S. Chatterjee, *J. Biol. Chem.*, 269:879–882 (1994)) leading to cell differentiation in human leukemic (HL-60) cells and insulin signaling (P. Peraldi et al., *J. Biol. Chem.*, 271:13018–13022 (1996)).

In addition to the biological roles of sphingomyelin and ceramide in signal transduction pathways involving cell regulation, recent evidence suggests that sphingomyelinases may be involved in the mobilization of cell surface cholesterol, in cholesterol ester synthesis, and in induction of low density lipoprotein (LDL) receptor activity. See S. Chatterjee, *Advances in Lipid Research*, 26:25–48 (1993). Recent evidence also supports a possible role of ceramide (a product of N-SMase activity) in programmed cell death and/or "apoptosis" and activation of the gene for nuclear factor (NF)-kB. See A. Alessenko and S. Chatterjee, *Mol. Cell. Biochem.*, 143:169–174 (1995). Sphingomyelinases are also believed to serve as a signal for various exogenous effectors such as antibiotics, drugs, and growth factors, which influence the normal physiology of cells.

A number of specific disorders have been associated with N-SMase. For example, N-SMase has been reported to be associated with insulin resistant diabetes and obesity. See Speigel et al., *J. Biol. Chem.*, 1996. N-SMase is also associated with malaria. The development of the malaria parasite plasmodium requires N-SMase. See Lauer et al., *Proc. Nat. Acad. Sci. (USA)*, 1995. N-SMase also is involved in liver cell proliferation. See Alessenko, Chatterjee, *Mol. Cell Biochem.*, 143:169–174 (1995).

Thus, methods for identifying agents which can modulate N-SMase activity would be highly useful. Moreover, methods for identifying pharmacological agents of interest by automated, high throughput drug screening have become increasing relied upon in a variety of pharmaceutical and biotechnology drug development programs. Unfortunately, however, requisite reagents for such high throughput screening assays to identify agents potentially useful in treatment of N-SMase associated disorders are not readily available. For example, current methods for procuring N-SMase include isolation of the protein from substantial quantities of urine. See, for example, S. Chatterjee, *J. Biol. Chem.*, 264(21):12554 (1989).

It thus would be desirable to have a convenient source of N-SMases. It also would be desirable to have agents that can modulate N-SMase activity. It would be further desirable to have effective assays for identifying compounds that have the potential to modulate N-SMase activity or to diagnose or treat disorders relating to N-SMase.

SUMMARY OF THE INVENTION

The present invention provides isolated nucleic acids that encode human neutral sphingomyelinases (N-SMase) and N-SMase fragments and derivatives capable of hybridizing to such N-SMase-encoding nucleic acids. cDNA (SEQ ID NO:1) encoding human N-SMase has been isolated and expressed to provide recombinant N-SMase having an apparent molecular weight of 44 kDa.

The invention ftnther provides isolated recombinant human neutral sphingomyelinase (N-SMase) and N-SMase fragments and derivatives.

The invention also provides novel assays for identifying compounds useful in the diagnosis or treatment of human neutral sphingomyelinase related disorders. Preferred compounds identified through assays of the invention can modulate, particularly inhibit, human neutral sphingomyelinase activity.

A variety of such assays are provided including, e.g., cleavage assays, direct binding assays, as well as assays that identify a particular domain function. A preferred assay of the invention comprises providing 1) an isolated human neutral sphingomyelinase or a fragment or derivative thereof, 2) a human neutral sphingomyelinase cleavage target such as sphingomyelin, and 3) a candidate pharmacological agent potentially useful in the diagnosis or treatment of disease associated with human neutral sphingomyelinase, which agents 1), 2) and 3) are typically assayed in admixture. Those agents are suitably treated under conditions whereby, but for the presence of the candidate pharmacological agent, the N-SMase or fragment or derivative thereof selectively cleaves the cleavage target to yield a cleavage product such as ceramide. The agents are then analyzed for the presence of the cleavage product, wherein the absence or reduced concentration (e.g. relative to control, i.e. same mixture of agents 1) and 2) but without the candidate agent 3)) of the cleavage product indicates that the candidate pharmacological agent is capable of modulating N-SMase activity, particularly inhibition of sphingomyelin cleavage activity.

Agents identified through assays of the invention will have potential for use in a number of therapeutic applications, especially to modulate, particularly inhibit, expression or activity of human neutral sphingomyelinase in particular cells. Specific disorders that potentially could be treated by administration of pharmacological agents identified through assays of the invention include inflammatory disorders such as arthritis and osteoarthritis, treatment of obesity and diabetes, treatment of malignancies, and treatment of HIV. Identified agents also may be useful for treatment of cirrhosis of the liver and other liver diseases, to increase human plasma low density lipoproteins receptors (to thereby reduce excessive cholesterol levels of a subject), and for treatment of atherosclerosis.

Identified agents also may be useful for in vitro fertilization applications, particularly to improve viability and/or effective lifetime of sperm or seminal fluid samples during storage. Identified agents also may be useful to treat or inhibit undesired vascular restensosis e.g. subsequent to arterial plaque removal. Identified agents also may be useful in the treatment of central nervous system disorders such as treatment of depression, schizophrenia and Alzheimer's disease, and treatment or prevention or inhibition of neurodegeneration. Identified agents also may be useful to prevent transmission of malaria by application of the agent to areas frequented by malaria carriers to thereby prevent development of the parasite plasmodium.

The invention further provides methods to modulate expression or activity of N-SMase in particular cells through administering to a patient in need thereof a therapeutically effective amount of human neutral sphingomyelinase or N-SMase fragment or derivative thereof or a nucleic acid encoding same. Preferably, an N-SMase fragment or derivative or corresponding nucleic acid is administered that contains only selected domains to thereby modulate N-SMase activity as desired and without effects associated with the deleted or otherwise altered domain(s). For instance, as discussed in more detail below, it will be generally preferred the TSLKVPA domain of N-SMase or corresponding nucleic acid sequence will not be present in functional form in administered peptides or nucleic acids.

Such therapeutic methods can be employed to treat subjects susceptible to (i.e. prophylactic treatment) or suffering from N-SMase related disorders including e.g. inflammatory disorders such as arthritis and osteroarthritis, Crohn's disease, treatment of obesity and diabetes, treatment of malignancies, particularly cancers including susceptible solid tumors, treatment of HIV, treatment of renal failure, and to prevent or inhibit transmission of malaria. N-SMase or fragments or derivatives thereof, and nucleic acids encoding same of the invention, also can be used for treatment of cirrhosis of the liver and other liver diseases, and to increase human plasma low density lipoproteins (LDL) receptors and to thereby reduce excessive cholesterol levels. N-SMase or fragments or derivatives thereof, and nucleic acids encoding same, also may be used for treatment of atherosclerosis.

N-SMase or fragments or derivatives thereof, and nucleic acids encoding same, also may be used for in vitro fertilization applications, particularly to improve viability and/or effective lifetime of sperm or seminal fluid samples during storage. In this aspect, the invention provides sperm or seminal fluid in combination with an N-SMase fragment or derivative to thereby provide enhanced viability or lifetime of samples during the storage period. The sperm or seminal fluid sample may be human, or of other mammal such as horse, cattle or other livestock.

N-SMase or fragments or derivatives, and nucleic acids encoding same, can be further employed to treat or inhibit undesired vascular restensosis e.g. subsequent to arterial plaque removal, and the treatment of central nervous system disorders such as treatment of depression, schizophrenia and Alzheimer's disease, and treatment or prevention or inhibition of neurodegeneration.

N-SMase or fragments or derivatives, and nucleic acids encoding same, particularly fragment or derivatives and nucleic acids that inhibit N-SMase activity, also may be administered to treat a patient, particularly a human, suffering from or susceptible to cardiac disease where LV dysfunction occurs, including a patient, particularly a human, suffering from or susceptible to heart failure.

Other aspects of the invention are disclosed infra.

BRIEF DESCRIPTION OF THE DRAWINGS

FIG. 1 shows a nucleotide sequence (SEQ ID NO:1) of isolated cDNA encoding human N-SMase.

FIG. 2 shows the deduced amino acid sequence (SEQ ID NO:2) of human N-SMase. ♦ N-glycosylation site, ● tyrosine kinase phosphorylation site, ♣ protein kinase phosphoryolation sites, ♥ casein kinase II phosphorylation sites, ∇ cyclic AMP and cyclic GMP dependent protein phosphorylation sites, underline: myristoylation sites, * stop codon.

FIG. 4A shows a Coomassie blue staining and FIG. 4B shows Western immunoblot analysis.

FIG. 6A shows tissue distribution of N-SMase. FIG. 6B shows transcript size of human kidney N-SMase.

FIG. 8A shows control cells. FIG. 8B shows PVS-SPOT. FIG. 8C shows PHH1.

DETAILED DESCRIPTION OF THE INVENTION

Figure 3:
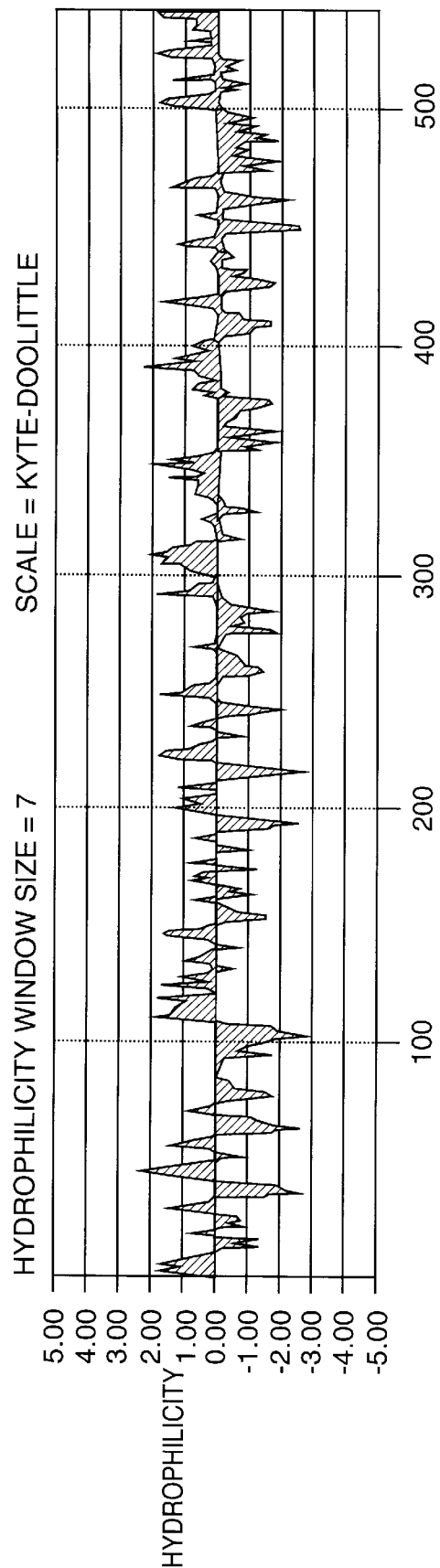
FIG. 3 shows the hydropathy plot analysis of N-SMase.

We have now isolated cDNA encoding a human N-SMase. This cDNA is represented by SEQ ID NO:1 (FIG. 1) and encodes a protein that when expressed in E. coli cells has an apparent molecular weight of 44 kDa as determined by polyacrylamide gel electrophoresis using sodium laurylsarocine. That recombinant protein is bound by an antibody against the 92 kDa native N-SMase. Protein was also expressed in Cos-7 cells. The isolated and purified recombinant N-SMase has been shown to have N-SMase activity. See, for instance, the results disclosed in Example 1 which follows.

As discussed above, the ability to regulate N-SMase activity in a particular environment is very important. Too high a level of N-SMase or conversely too low a level of N-SMase can result in undesired effects. For example, excessively high N-SMase levels can result in apoptosis, while excessively low levels of N-SMase can result in lack of cell proliferation or lack of LDL receptors. Similarly, N-SMase expression in one cell type can be desirable in leading to more efficient cholesterol processing, whereas its expression in another cell type can be undesirable.

As discussed above, the invention provides methods to modulate, including inhibition of, expression or activity of N-SMase in particular cells. For example, one can use a N-SMase nucleic acid segment operably linked to a N-SMase promoter to selectively direct it to desired cells. As another example, one can administer a N-SMase protein or fragment or derivative to modulate N-SMase activity.

The invention further provides isolated N-SMase having an amino acid sequence represented by SEQ ID NO:2 (FIG. 2), as well as fragments or derivatives thereof.

The term "fragment" or "derivative" when referring to an N-SMase protein means proteins or polypeptides which retain essentially the same biological function or activity as the protein of SEQ ID NO:2. For example, the N-SMase fragments or derivatives of the present invention maintain at least about 50% of the activity of the protein of SEQ ID NO:2, preferably at least 75%, more preferably at least about 95% of the activity of the protein of SEQ ID NO:2, as determined e.g. by a standard activity gel assay such as the assay disclosed in Example 1, part 6, which follows and includes measuring activity of the N-SMase peptide using [$^{14}$C]-sphingomyelin.

Fragments or derivatives as the term is used herein can include competitors of the native N-SMase with respect to a particular N-SMase domain activity. However, the fragment or derivative shows an overall similarity to N-SMase in other areas as explained herein.

An N-SMase fragment or derivative of the invention may be (i) a peptide in which one or more of the amino acid residues are substituted with a conserved or non-conserved amino acid residue (preferably a conserved amino acid residue) and such substituted amino acid residue may or may not be one encoded by the genetic code, or (ii) a peptide in which one or more of the amino acid residues includes a substituent group, or (iii) a peptide in which the mature protein is fused with another compound, such as a compound to increase the half-life of the polypeptide (for example, polyethylene glycol). Thus, an N-SMase fragment or derivative includes a proprotein which can be activated by cleavage of the proprotein portion to produce an active mature polypeptide.

The protein fragments and derivatives of the invention are of a sufficient length to uniquely identify a region of N-SMase. N-SMase fragments and derivatives thus preferably comprise at least 8 amino acids, usually at least about 12 amino acids, more usually at least about 15 amino acids, still more typically at least about 30 amino acids, even more typically at least about 50 or 70 amino acids. Preferred N-SMase fragments or derivatives of the invention include those that have at least about 70 percent homology (sequence identity) to the protein of SEQ ID NO:2, more preferably about 80 percent or more homology to the protein of SEQ ID NO:2, still more preferably about 85 to 90 percent or more homology to the protein of SEQ ID NO:2.

N-SMase and fragments and derivatives thereof of the invention are "isolated", meaning the protein or peptide constitutes at least about 70%, preferably at least about 85 %, more preferably at least about 90% and still more preferably at least about 95% by weight of the total protein in a given sample. A protein or peptide of the invention preferably is also at least 70% free of immunoglobulin contaminants, more preferably at least 85% free, still more preferably at least 90% free and even more preferably at least 95% free of immunoglobulin contaminants. The N-SMase fragments and derivatives may be present in a free state or bound to other components, e.g. blocking groups to chemically insulate reactive groups (e.g. amines, carboxyls, etc.) of the peptide, or fusion peptides or polypeptides (i.e. the peptide may be present as a portion of a larger polypeptide).

As discussed above, N-SMase nucleic acid fragments and derivatives are also provided. Those fragments and derivatives are of a length sufficient to bind to the sequence of SEQ ID NO:1 under the following moderately stringent conditions (referred to herein as "normal stringency" conditions): use of a hybridization buffer comprising 20% formamide in 0.8M saline/0.08M sodium citrate (SSC) buffer at a temperature of 37° C. and remaining bound when subject to washing once with that SSC buffer at 37° C.

Preferred N-SMase nucleic acid fragments and derivatives of the invention will bind to the sequence of SEQ ID NO:1 under the following highly stringent conditions (referred to herein as "high stringency" conditions): use of a hybridization buffer comprising 20% formamide in 0.9M saline/0.09M sodium citrate (SSC) buffer at a temperature of 42° C. and remaining bound when subject to washing twice with that SSC buffer at 42° C.

These nucleic acid fragments and derivatives preferably should comprise at least 20 base pairs, more preferably at least about 50 base pairs, and still more preferably a nucleic acid fragment or derivative of the invention comprises at least about 100, 200, 300, 400, 500 or 800 base pairs. In some preferred embodiments, the nucleic acid fragment or derivative is bound to some moiety which permits ready identification such as a radionucleotide, fluorescent or other chemical identifier.

N-SMase will have a number of functional domains, e.g., a TNF-α 55 kDa receptor/Fas Apo(o)-1 domain, the sterol regulator element binding protein (SREBP) domain, etc. N-SMase of FIG. 2 also has a domain (TSLKVPA, residues 258–264 of FIG. 1; SEQ ID NO:3) homologous to the Staphyococcal enterotoxin-B peptide domain (RSITVRV; SEQ ID NO:4), which domain has been reported to elicit toxic effects in human kidney cells. Accordingly, preferred N-SMase fragments and derivatives do not include that TSLKVPA domain in functional form. Other N-SMase domains can be readily identified by standard techniques such as deletion analysis.

In a similar manner, one can readily identify a deletion, addition or substitution that will inactivate a particular domain, e.g. by simply testing a fragment or derivative with altered domain to determine if the fragment or derivative exhibits activity associated with the altered domain. Any of a variety of tests can be employed, such as e.g. the in vitro tests of Example 1 which follows.

Thus, an N-SMase protein or nucleic acid fragment or derivative can be employed that contains only specific domains and can be administered to a subject such as a mammal to modulate N-SMase activity in targeted cells as desired.

Preferred N-SMase protein and nucleic acid fragments and derivatives include at least one functional domain region, e.g. the TNF-α binding domain, the SREBP domain or the sphingomyelin cleavage domain. Particularly preferred fragments and derivatives comprise one or more conserved peptides or corresponding nucleic acid sequences of at least one functional domain region.

Several apparent isoforms of human N-SMase exist that can be distinguished based on physical-chemical criteria, including electrophoretic migration rates, reactions against antibody of N-SMase and reactions to metals including copper, lithium and magnesium. The N-SMase and fragments and derivatives thereof of the present invention, and nucleic acids encoding same, include such isoforms.

Isolated N-SMase and peptide fragments or derivatives of the invention are preferably produced by recombinant methods. See the procedures disclosed in Example 1 which follows. A wide variety of molecular and biochemical methods are available for generating and expressing the N-SMase of the present invention; see e.g. the procedures disclosed in *Molecular Cloning, A Laboratory Manual* (2nd Ed., Sambrook, Fritsch and Maniatis, Cold Spring Harbor), *Current Protocols in Molecular Biology* (Eds. Aufubel, Brent, Kingston, More, Feidman, Smith and Stuhl, Greene Publ. Assoc., Wiley-Interscience, New York, N.Y. 1992) or other procedures that are otherwise known in the art. For example, N-SMase or fragments thereof may be obtained by chemical synthesis, expression in bacteria such as *E. coli* and eukaryotes such as yeast, baculovirus, or mammalian cell-based expression systerns, etc., depending on the size, nature and quantity of the N-SMase or fragment. The use of mammalian-based expression systems, particularly human, is particularly preferred where the peptide is to be used therapeutically.

Nucleic acids encoding the novel N-SMase of the present invention and fragments and derivatives thereof may be part of N-SMase expression vectors and may be incorporated into recombinant cells for expression and screening, transgenic animals for functional studies (e.g. the efficacy of candidate drugs for disease associated with expression of a N-SMase), etc. Nucleic acids encoding N-SMase containing proteins are isolated from eukaryotic cells, preferably human cells, by screening cDNA libraries with probes or PCR primers derived from the disclosed N-SMase cDNAs.

The nucleic acids of the present invention are isolated, meaning the nucleic acids comprise a sequence joined to a nucleotide other than that which it is joined to on a natural chromosome and usually constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

The nucleic acids of the present invention find a wide variety of applications including: use as translatable transcripts, hybridization probes, PCR primers, therapeutic nucleic acids, etc.; use in detecting the presence of N-SMase genes and gene transcripts; use in detecting or amplifying nucleic acids encoding additional N-SMase homologs and structural analogs; and use in gene therapy applications.

For example, N-SMase nucleic acids can be used to modulate cellular expression or intracellular concentration or availability of active N-SMase. Thus, for example, N-SMase has been shown to be involved in liver cell proliferation (Alessenko and Chattedee, *Mol. Cell. Biochem.* 143:119–174, (1995)), and thus N-SMase nucleic acids may be used to treat liver diseases such as cirrhosis.

To inhibit N-SMase activity, nucleic acid encoding a competitor or an antagonist can be administered to a subject. One preferred embodiment employs nucleic acid encoding an N-SMase derivative that acts as a competitor or an antagonist. For example, dependent upon the N-SMase activity desired to be inhibited, the N-SMase domain responsible for that activity can be appropriately altered (e.g. deleted or mutated), whereby the protein will still display the desired activity, but will not exhibit the undesired activity. Moreover, the altered protein can compete with the native N-SMase to thereby inhibit the undesired activity.

Further, to reduce N-SMase activity, nucleic acids capable of inhibiting translation of N-SMase also may be administered. These nucleic acids are typically antisense: single-stranded sequences comprising complements of the disclosed relevant N-SMase fragment-encoding nucleic acid. Antisense modulation of the expression of a given N-SMase fragment containing protein may employ N-SMase fragment antisense nucleic acids operably linked to gene regulatory sequences. Cells are transfected with a vector comprising an N-SMase fragment sequence with a promoter sequence oriented such that transcription of the gene yields an antisense transcript capable of binding to endogenous N-SMase fragment containing protein encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a given N-SMase fragment containing protein may be administered to the target cell, in or temporarily isolated from a host, at a concentration that results in a substantial reduction in expression of the N-SMase.

The N-SMase nucleic acids are introduced into the target cell by any method which will result in the uptake and expression of the nucleic acid by the target cells. These can include vectors, liposomes, naked DNA, adjuvant-assisted DNA, catheters, etc. Vectors include chemical conjugates such as described in WO 93/04701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpes virus vectors such as a herpes simplex I virus (HSV) vector [A. I. Geller et al., *J. Neurochem*, 64:487 (1995); F. Lim et al., in *DNA Cloning: Mammalian Systems*, D. Glover, Ed. (Oxford Univ. Press, Oxford England) (1995); A. I. Geller et al., *Proc Natl. Acad. Sci.: U.S.A.*:90 7603 (1993); A. I. Geller et al., *Proc Natl. Acad. Sci USA*: 87:1149 (1990)], Adenovirus Vectors [LeGal LaSalle et al., *Science*, 259:988 (1993); Davidson, et al., *Nat. Genet.*, 3:219 (1993); Yang et al., *J. Virol.*, 69: 2004 (1995)] and Adeno-associated Virus Vectors [Kaplitt, M. G., et al., *Nat. Genet.*, 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $Ca_3(PO_4)_2$ precipitation, DEAE dextran, electroporation, protoplast fusion, lipofecton, cell microinjection, and viral vectors.

The vector can be employed to target essentially any desired target cell, such as a glioma. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell (Bobo et al., *Proc. Natl. Acad. Sci. USA*, 91:2076–2080 (1994); Morrison et al., *Am. J. Physiol.*, 266: 292–305 (1994)). Other methods that can be used include catheters, intravenous, parenteral, intraperitoneal and subcutaneous injection, and oral or other known routes of administration.

The invention provides efficient screening methods to identify pharmacological agents or lead compounds for agents which modulate, e.g. interfere with or increase an N-SMase activity. The methods are amenable to automated, cost-effective high throughput drug screening and have immediate application in a broad range of pharmaceutical drug development programs.

A wide variety of assays are provided including, e.g., cleavage assays, direct binding assays as well as assays to identify a particular domain function.

A preferred assay mixture of the invention comprises at least a portion of the N-SMase capable of cleaving a N-SMase cleavage target, e.g. sphingomyelin. An assay mixture of the invention also comprises a candidate pharmacological agent. Generally a plurality of assay mixtures are run in parallel with different candidate agent concentrations to obtain a differential response to the various concentrations. Typically, one of these assay mixtures serves as a negative control, i.e. at zero concentration or below the limits of assay detection. Candidate agents encompass numerous chemical classes, though typically they are organic compounds and preferably small organic compounds. Small organic compounds suitably may have e.g. a molecular weight of more than about 50 yet less than about 2,500. Candidate agents may comprise functional chemical groups that interact with proteins and/or DNA.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced.

Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc.

A variety of other reagents may also be included in the mixture. These include reagents such as salts, buffers, neutral proteins, e.g. albumin, detergents, etc. which may be used to facilitate optimal protein-protein and/or protein-nucleic acid binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the N-SMase or fragment or derivative thereof cleaves the cleavage target. The mixture components can be added in any order that provides for the requisite bindings. Incubations may be performed at any temperature which facilitates optimal binding, typically between 4° and 40° C., more commonly between 15° and 40° C. Incubation periods are likewise selected for optimal binding but also minimized to facilitate rapid, high throughput screening, and are typically between 0.1 and 10 hours, preferably less than 5 hours, more preferably less than 2 hours.

After incubation, the presence or absence of the cleavage product is detected by any convenient way. For cell-free type assays, the cleavage target may be bound to a solid substrate and the cleavage product labelled, e.g., radiolabelled. A separation step can be used to separate the bound target from unbound cleavage product. The separation step may be accomplished in a variety of ways known in the art. The solid substrate may be made of a wide variety of materials and in a wide variety of shapes, e.g. microtiter plate, microbead, dipstick, resin particle, etc. The substrate is chosen to maximize signal to noise ratios, to minimize background binding, to facilitate washing and to minimize cost.

Separation may be effected for example, by removing a bead or dipstick from a reservoir, emptying or diluting a reservoir such as a microtiter plate well, rinsing a bead (e.g. beads with iron cores may be readily isolated and washed using magnets), particle, chromatographic column or filter with a wash solution or solvent. Typically, the separation step will include an extended rinse or wash or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc. may exploit a polypeptide specific binding reagent such as an antibody or receptor specific to a ligand of the polypeptide.

As mentioned, detection may be effected in any convenient way, and for cell-free assays, one of the components usually comprises or is coupled to a label. Essentially any label can be used that provides for detection. The label may provide for direct detection as radioactivity, luminescence, optical or electron density, etc. or indirect detection such as an epitope tag, an enzyme, etc. The label may be appended to a reagent or incorporated into the peptide structure, e.g. in the case of a peptide reagent, a methionine residue comprising a radioactive isotope of sulfur.

A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters.

The assays of the invention are particularly suited to automated high throughput drug screening. In a particular embodiment, an automated mechanism, e.g. a mechanized arm, retrieves and transfers a microtiter plate to a liquid dispensing station where measured aliquots of each of an incubation buffer and a solution comprising one or more candidate agents are deposited into each designated well. The arm then retrieves and transfers to and deposits in designated wells a measured aliquot of a solution comprising a N-SMase protein or fragment or derivative thereof as well as solutions of other reagents such as a cleavage target. Thereafter, the arm transfers the microtiter plate to an analysis station where the reaction mixture can be analyzed for the presence or absence of various reaction products.

A preferred assay is disclosed in Example 2 which follows and which includes application of labeled sphingomyelin ([$^{14}$C]sphingomyelin) to a solid substrate such as a multi-well tray together with N-SMase.

As discussed above, N-SMase or fragments or derivatives thereof, and nucleic acids encoding same, also may be used for in vitro fertilization applications, particularly to improve viability and/or effective lifetime of sperm or seminal fluid samples during storage.

In this aspect, the invention also provides stored samples of human or other mammal such as cattle or horse sperm or seminal fluid in combination with an N-SMase fragment or derivative to thereby provide enhanced viability or lifetime of samples during the storage period.

For example, a sperm or seminal fluid storage unit of the invention may suitably comprise an N-SMase fragment or derivative of the invention in combination with a sperm or seminal fluid sample. That mixture also may optionally comprise a buffer or diluent as may be used with such samples. The N-SMase fragment or derivative preferably will be present in an amount sufficient to enhance the viability of lifetime of the sperm or seminal fluid sample during the storage period. Such storage effective amount amounts can be readily determined empirically for the particular N-SMase fragment or derivative employed. Storage effective amounts suitably may be at least about 0.01 weight percent of N-SMase derivative or fragment thereof based on total weight of the storage sample, more preferably at least about 0.05 weight percent. The sperm or seminal fluid sample may be human or of other mammal, e.g. horse, cattle or other livestock sample. The storage unit may suitably be a sterile cryovial or other vessel as conventionally employed to store sperm and seminal fluid.

The proteins and nucleic acids and fragments and derivatives thereof of the invention also may be used to generate immune responses. For example, it has been found that in certain instances where inappropriate expression of a self-protein is occurring an immune reaction can be useful. The nucleic acid permits the creation of unique peptides that can generate such a reaction. The characteristics needed to generate a peptide that will induce a MHC class I or II reaction are known and suitable peptides having such characteristics can be readily prepared based upon the present disclosure.

Antibodies also can be prepared that will bind to one or more particular domains of a peptide of the invention and can be used to modulate N-SMase activity.

Moreover, administration of an antibody against N-SMase or fragment or derivative thereof, preferably monoclonal or monospecific, to mammalian cells (including human cells) can reduce or abrogate TNF-$\alpha$ induced cell death (apoptosis) and the invention includes such therapeutic methods. In such methods, antibody against N-SMase can be administered to a mammal (including a human) by known procedures. It has been specifically found that apoptosis of human leukemic (HL-60) cells expressing N-SMase was abrogated by treatment with antibody against N-SMase.

The preferred therapeutic methods of the invention (which include prophylactic treatment) in general comprise administration of a therapeutically effective amount of N-SMase or fragment or derivative thereof, or nucleic acid encoding same, to an animal in need thereof, including a mammal, particularly a human. Such treatment will be suitably administered to subjects, particularly humans, suffering from or susceptible to one of the above discussed disorders, including inflammatory disorders such as arthritis, osteroarthritis and Crohn's disease, obesity, diabetes, malignancies, particularly cancers including susceptible solid tumors, HIV, liver disorders including cirrhosis, excessive cholesterol levels, renal failure, cholesteryl ester storage disorder, cardiac disease associated with LV dysfunction, atherosclerosis, undesired vascular restensosis, neurodegeneration, and central nervous system disorders such as depression, schizophrenia and Alzheimer's disease.

For therapeutic applications, peptides and nucleic acids of the invention may be suitably administered to a subject such as a mammal, particularly a human, alone or as part of a pharmaceutical composition, comprising the peptide or nucleic acid together with one or more acceptable carriers thereof and optionally other therapeutic ingredients. The carrier(s) must be "acceptable" in the sense of being compatible with the other ingredients of the formulation and not deleterious to the recipient thereof.

The pharmaceutical compositions of the invention include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and in liposomes, and may be prepared by any methods well know in the art of pharmacy. See, for example, *Remington's Pharmaceutical Sciences*, Mack Publishing Company, Philadelphia, Pa. (17th ed. 1985).

Such preparative methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and nonaqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Application of the subject therapeutics often will be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way. Systemic administration of a nucleic acid using lipofection, liposomes with tissue targeting (e.g. antibody) may also be employed.

It will be appreciated that actual preferred amounts of a given peptide or nucleic acid of the invention used in a given therapy will vary to the particular active peptide or nucleic acid being utilized, the particular compositions formulated, the mode of application, the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests.

The present invention is further illustrated by the following Examples. These Examples are provided to aid in the understanding of the invention and are not construed as a limitation thereof.

EXAMPLE 1

Cloning and Expression of Human Neutral Sphingomyelinase

1. Purification of Human Neutral Sphingomyelinase and Preparation of Antibodies.

Neutral sphingomyelinase (N-SMase) was prepared from human urine and polyclonal antibodies against that enzyme were raised in rabbits as described previously by S. Chatterjee et al., *J. Biol. Chem.*, 264:12,534–12,561 (1989). Monospecific polyclonal antibodies against N-SMase were prepared by appropriate immuno-affinity absorption techniques as described in *J. Biol. Chem.*, 264:12,534–12,561 (1989).

2. Screening of cDNA Library.

The human kidney library was purchased from Clontech (Palo Alto, Calif.) and was screened using anti-N-SMase described above according to the manufacturers protocol. Briefly, the $\lambda$gt11 phage was plated at $3 \times 10^4$ pfu/150 mm plate on a lawn of *E.Coli* strain y1090r. Incubation was carried out at 42° C. for 3.5 hrs to allow lytic phage growth. Then, a filter saturated with 10 mM IPTG was placed on top of the plate and incubated overnight at 37° C. Next, the filter was blocked with a solution of 5% non-fat dry milk for 1 hr at room temperature. Next, the filter was incubated with antibody against N-SMase at 1:200 dilution at room temperature overnight, and signal was detected by enhanced chemiluminence technique (ECL, Amersham). Sixty-three clones were obtained by screening $1 \times 10^6$ $\lambda$gt11 phage clones. The most intense clones of cells were subjected to secondary and tertiary screening. All positive clones were subject to PCR to identify their insert size. Finally, a clone containing the longest insert (3.7 kb) referred to as $\lambda^{32}$-1 was used for further analysis by subcloning, sequencing and expression.

3. Preparation of Fusion Proteins.

The protocol as described by the manufacturer's manual (Biotech, #5, 1992, pg. 636) was followed. By this procedure, the host growing in the logarithmic phase was infected with phage and incubated for 2 hr at 30° C. Next, IPTG (10 mM) was added and incubation continued at 37° C. The cell cultures were removed at 0, 15 min., 30 min., 45 min., 1 hr, 2 hr, 4 hr and 24 hr. The cells were centrifuged, washed with PBS, and stored frozen for N-SMase activity measurement.

4. Subcloning and sequencing of N-SMase cDNA.

First, the $\lambda^{32}$-1 DNA was purified with the Magical Lambda preps DNA purification system from Promega by following the manufacturer's manual. Then, it was digested with the restriction endonucleosidase EcoRI. The 3.7 kb insert was gel purified and subcloned into the EcoRI site of the vector pBluescriptII-SK (Stratagene, La Jolla, Calif.). The plasmid, thus generated was termed pBC32-2, and was purified using QIAGEN's DNA purification system. The N-SMase cDNA insert was sequenced with Sequenase using T7 and T3 primers by automatic sequence machine Model 373A (Applied Biosystems).

5. Transient Expression of N-SMase in Cos-7 Cells.

To put N-SMase cDNA into a transient expression vector, the pBC32-2 was double digested with restriction endonucleosidases NotI and Sal1. The 3.6 kb insert containing N-SMase was gel purified and inserted into a transient expression vector PSV-SPOT-1 (BRL). Thus, a plasmid called $pHH_1$ was constructed.

To transfect Cos-7 cells with $pHH_1$ and mock vector, $3 \times 10^5$ Cos-1 cells/plate in a p100 plate in 8 ml of Dulbecco's modified Eagle's medium (D-MEM) were seeded with 10% FCS (Bethesda Research Laboratory; BRL). Cells were incubated in a 10% $CO_2$ 37° C. incubator until they are 80% confluent. The cells were then transfected with 10 µg of purified pHHI (QIAGEN) using LipoFectamine™ (BRL) in medium. Medium was changed after 5 hours of incubation. Finally, the cells were harvested at various time points (16 hr, 24 hr, 36 hr, and 48 hr, post transfection) by centrifugation at 1500×g for 10 min., washed with phosphate buffered saline (PBS) and stored frozen at −20° C.

6. Activity Gel Assay of N-SMase Expression in Transfected Cos-7 Cells.

Both the bacterial cells and Cos-7 cells transfected with N-SMase cDNA were homogenized in Tris-glycine buffer (pH 7.4) containing 0.1% cutscum. The samples were mixed vigorously and sonicated for 10 sec. Next, the samples were transferred to a 4° C. incubator and shaken for about 2 hours. Every hour, the samples were sonicated again on ice and further shaken. Subsequently, the samples were centrifuged at 10,000×g for 10 min. The supernatants were collected, the protein content was measured and subjected to polyacrylamide gel electrophoresis using sodium laurylsarcosine. Subsequent to electrophoresis, the gel was sliced into several pieces and the activity of N-SMase was measured using [$^{14}$C]-sphingomyelin as a substrate (see T. Taki and S. Chatterjee, *Analyt. Biochem.*, 224:490–493 (1995)).

7. Measurement of Sphingomyelinase Activity in Aortic Smooth Muscle Cells Transiently Transfected with N-SMase cDNA.

The activity of sphingomyelinase was measured in aortic smooth muscle cell extracts transiently transfected with pSVSPOT (mock cDNA) and pHH1 (cDNA for N-SMase) as shown previously in P. Ghosh and S. Chatterjee, *J. Biol. Chem.*, 262:12,550–12,556 (1987)). Briefly, the cell extracts (100 μg protein) were incubated with cutscum, MgCl$_2$, human serum albumin and Tris glycine buffer (pH 7.4) plus [$^{14}$C]-sphingomyelin (15,000 cpm) for 1 hr at 37° C. The reaction was terminated with 1 ml of 10% TCA and centrifuged. The supernatant was extracted with diethylether and the aqueous layer was withdrawn to measure radioactivity.

8. Reverse Transcriptase-Polymerase Chain Reaction.

Human kidney cells were seeded (1×10$^5$ cell/plate in p100 plates) and grown to confluence in complete medium with 10% fetal calf serum. Total RNA was isolated by acid guanidium thiocyanate-phenol-chloroform extraction. 1 μg of total RNA was used to synthesize first strand cDNA using 20 pmol random hexamer primer, 200 units moloney murine leukemia virus reverse transcriptase, 0.5 mM each of deoxynucleotide triphosphates (Clontech, Palo Alto, Calif.) in buffer containing 50 mM Tris-HCl, 75 mM KCl, 3 mM MgCl$_2$, and 0.5 units of RNAse inhibitor, pH 8.3 at 42° C. for 1 hour. 1 μl of 1:100 dilution of cDNA products was used to run PCR in 50 μl reaction mixture containing 0.2 mM each of dNTP, 2.0 units of Taq polymerase, 0.4 uM of each primers, 10 mM Tris HCl, 50 mM KCl, and 1.5 mM MgCl$_2$ (pH 8.3). The PCR was run for 35 cycles (30s at 94° C., 30s at 55° C. and 30s at 72° C.) using a Perkin-Elmer Thermocycler.

9. Northern Blot Analysis.

One set of sequence primers from pBC32-2, T3-2/4T3R5, as RT-PCR primer was selected to conduct RT-PCR as described above. The 18-mer primers had the following sequence: TTGCGGCACTATTAGGTG (SEQ ID NO:5) and CGCCAATGCCAAAACGTA (SEQ ID NO:6). A 465 bp specific product was obtained, and gel purified. 50 ng of this product was labeled with 25 μCi[α-$^{32}$P] dATP and 25 μCi [α-$^{32}$P] dCTP using Random hexamer primers (BRL). The specific activity of this probe was 1.88×10$^9$ cpm/μg. Next, the multiple tissue northern blot (Clontech; Palo Alto, Calif.) were hybridized with this probe(2×10) at 50° C. overnight with hybridization buffer. Next, the blots were washed twice in 2× SSC, 0.05 % SDS at room temperature for 30–40 min, then in 0.1× SSC and 0.05% SDS for 40 min. at 50° C. Finally, the blot was exposed to an x-ray film at −70° C. using two intensifying screens overnight.

10. Expression and Purification of Glutathione-S-Transferase (GST)-N-SMase Fusion Protein in *E.Coli*.

To prepare GST-N-SMase fusion protein, an expression plasmid pJK2, pBC32-2 was digested with BssHII and EcoRI. A 2793 bp insert representing N-SMase open reading frame that is missing 18 bp N-terminal sequence, was ligated with a phosphorylated BamHI-BssHII linker containing the N-terminal sequence of GATCCATGATGACATATCAC-GAAACGCGCGTTTCGTGATA TGTCATCATG (SEQ ID NO:7) and a pGEX4T-1 vector double digested with BamHI and EcoRI (Phamacia; Piscataway, N.J.). To express and purify GST-N-SMase fusion protein, plasmid pJK2 was transformed into *E.Coli* (HB101) cells. A single colony of HB101 [pJK2] was grown in 2× YTA medium at 30° C. until appropriate cell density (A600=1.5) was achieved. IPTG (0.1M) was added to induce fusion protein expression for 2 hours. Cells were harvested and the fusion protein was purified using Glutathione Sepharose-4B chromatography according to instructions provided by the manufacturer. N-SMase was released from the fusion protein by thrombin digestion. Such preparations were subjected to activity measurements and western immunoblot assays.

11. Coomassie Blue Staining and Western Immunoblot Assays of r-N-SMase.

20 μg of purified r-N-SMase was subjected to electrophoresis on 12.5% SDS-PAGE gel. One gel was stained with Coomassie blue according to standard protocol. Another gel were transferred onto a PVDF membrane. Next, the polyvinyldiflouride (PVDF) membrane was blocked with 1% bovine serum albumin in TBS-T, incubated with anti-N-SMase at a dilution of 1:200 and developed with horse radish peroxidase (see S. Chatterjee et al., *J. Biol. Chem.*, 264:12,534–12,561 (1989)).

12. Measurement of Apoptosis in Aortic Smooth Muscle Cells Transfected With cDNA for N-SMase.

Aortic smooth muscle cells transiently transfected with PVSPOT (mock cDNA) and pHH1 (cDNA for N-SMase) for 24 hours were solubilized and subjected to agarose gel electrophoresis (2 hr at 90 volts) for DNA fragamentation analysis.

Another set of cells transfected with cDNA were subjected to staining with the DNA-binding florochrome bis-benzimidine (Hoescht 323288; Sigma Chemical Co., St. Louis, Mo.). Briefly, transfected cells grown on glass cover slips were washed with PBS. The cells were fixed with 3% paraformaldehyde in PBS and incubated for 10 min at room temperature. The cells were washed with PBS and stained with 16 μg/ml of bis-benzimidine in PBS. After 15 min of incubation at room temperature, the samples were photographed. An Olympus BH$_2$ flourescence microscope with a BH$_2$-DMU U$_2$ UV mirror cube filter was used. Cells with three or more chromatin fragments were considered apoptotic.

The above-mentioned 3.7 kb nucleotide sequence of cDNA revealed an open reading frame size of 1197 base pairs which predicts a 397 amino acid polypeptide. The deduced amino acid sequence is shown in FIG. 2. The estimated protein molecular weight is approximately 44 kDa, the estimated pI is 4.93. There are several potential modification sites in this protein: 1 N-glycosylation site at amino acid position 353; 1 tyrosine phosphorylation site at 238; and 2 cyclic AMP and cyclic GMP dependent protein kinase phosphorylation sites at position 218 and 357. It also has four casein kinase II phosphorylation sites at 3, 33, 65 and 101. Five myristoylation sites at 28, 44, 205, 206 and 220 bases were also found. There are ten protein kinase-C phosphorylation sites at 38, 48, 164, 216, 217, 236, 251, 260, 323 and 355.

Hydropathy plot analysis of N-SMase (FIG. 3 of the drawings) indicates that there is no apparent transmembrane domain. The N-glycosylation site at amino acid position 353, tyrosine phosphorylation site at 238, as well as several other phosphorylation sites are presumably located on the exterior. Such sites may be subjected to further glycosylation and phosphorylation.

Figures 4A, 4B:
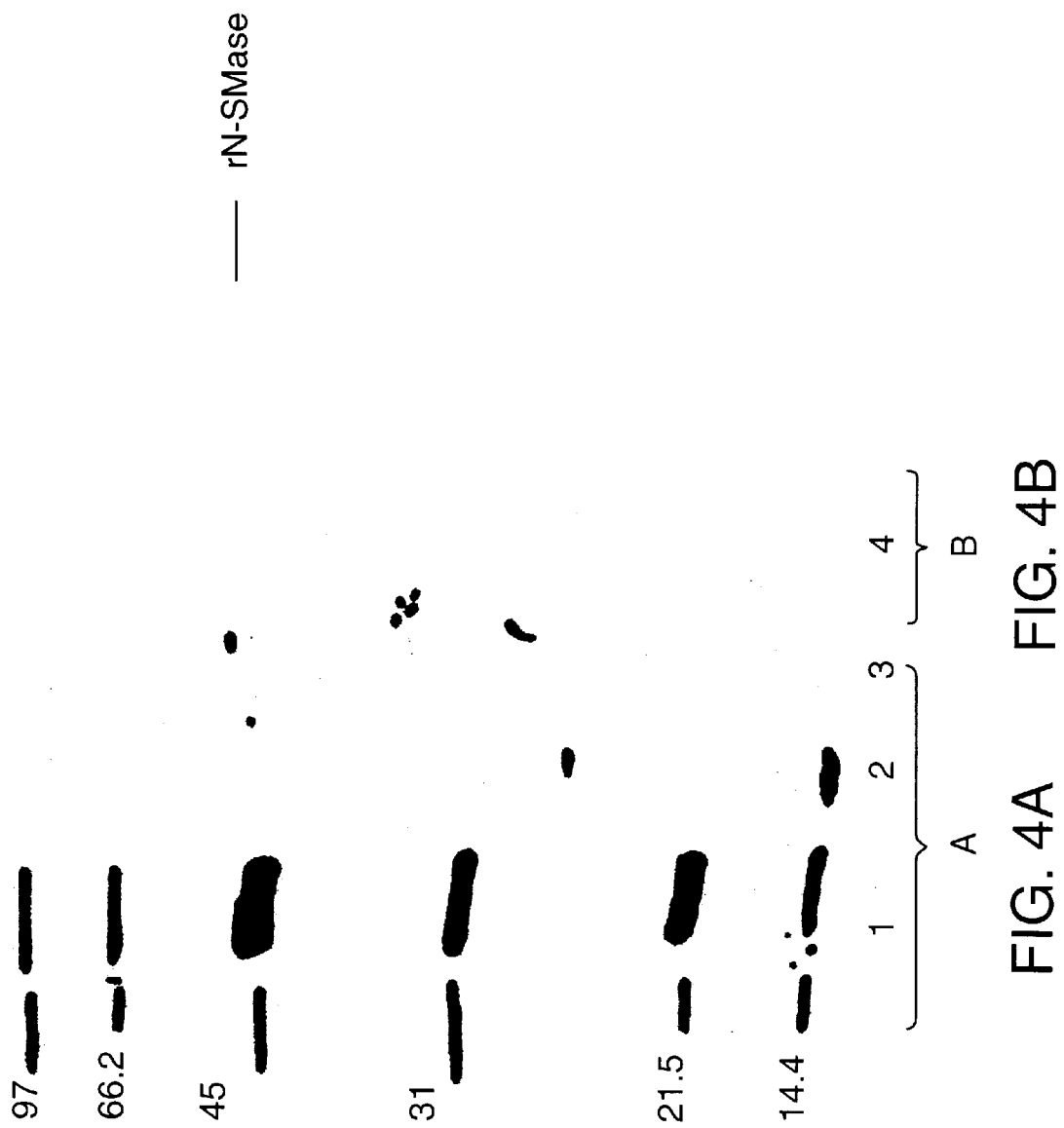
FIGS. 4A and 4B show gel electrophoretic analysis of recombinant N-SMase expressed in E. coli.

To confirm that the 3.7 kb cDNA does encode N-SMase with an apparent molecular weight of 44 kDa, constructs were made to fuse cDNA coding region with Glutathione-S-Transferase. Then, this plasmid was transformed into *E.coli* (HB101) to express and purify GST-N-SMase fusion protein. The expression of fusion protein was induced by IPTG (0.1M) for 2 hours. The fusion protein was purified using Glutathione Sepharose-4B chromatography. The fusion protein has an apparent molecular weight of 73 kDa. After thrombin digestion, it resolved into two bands, 29 kDa and 44 kDa which correspond to GST and N-SMase, respectively. After N-SMase was released from fusion protein by Glutathione Sepharose-4B chromatography, it resolved as a single band, having a molecular weight on the order of 44 kDa. This protein was recognized by antibody against human N-SMase. See FIGS. 4A and 4B. Affinity-purified recombinant N-SMase expressed in *E.coli* had activity on the order of 3.9 nmole/mg protein/2 h compared to mock cDNA transfected cells which had activity of 2.9 nmoles/mg protein/2 h).

Figure 5:
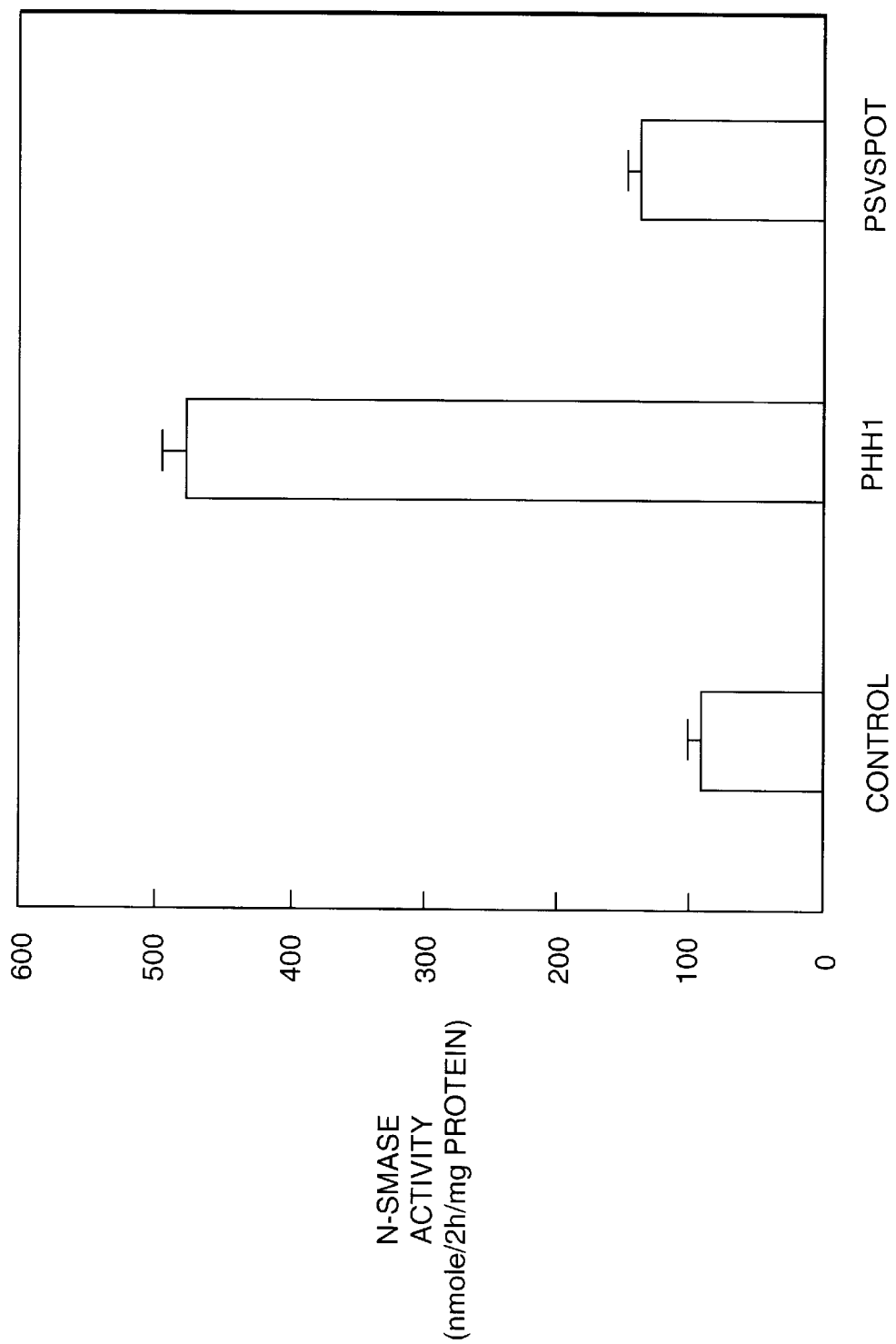
FIG. 5 shows transient expression of recombinant N-SMase in Cos-7 cells.

The results set forth in FIG. 5 of the drawings show that Cos-7 cells transfected with pHHI exhibited a 10-fold increase in N-SMase activity compared to cells transfected with mock vector pSPOT-1 24 hours post-transfection. The most active recombinant N-SMase had an apparent molecular weight of 100 kDa. Significant N-SMase activity in a descending order was observed in protein bands having apparent kDa of 130 and 74. Those results indicate that N-SMase undergoes multiple post-translational modification.

Figures 6A, 6B:
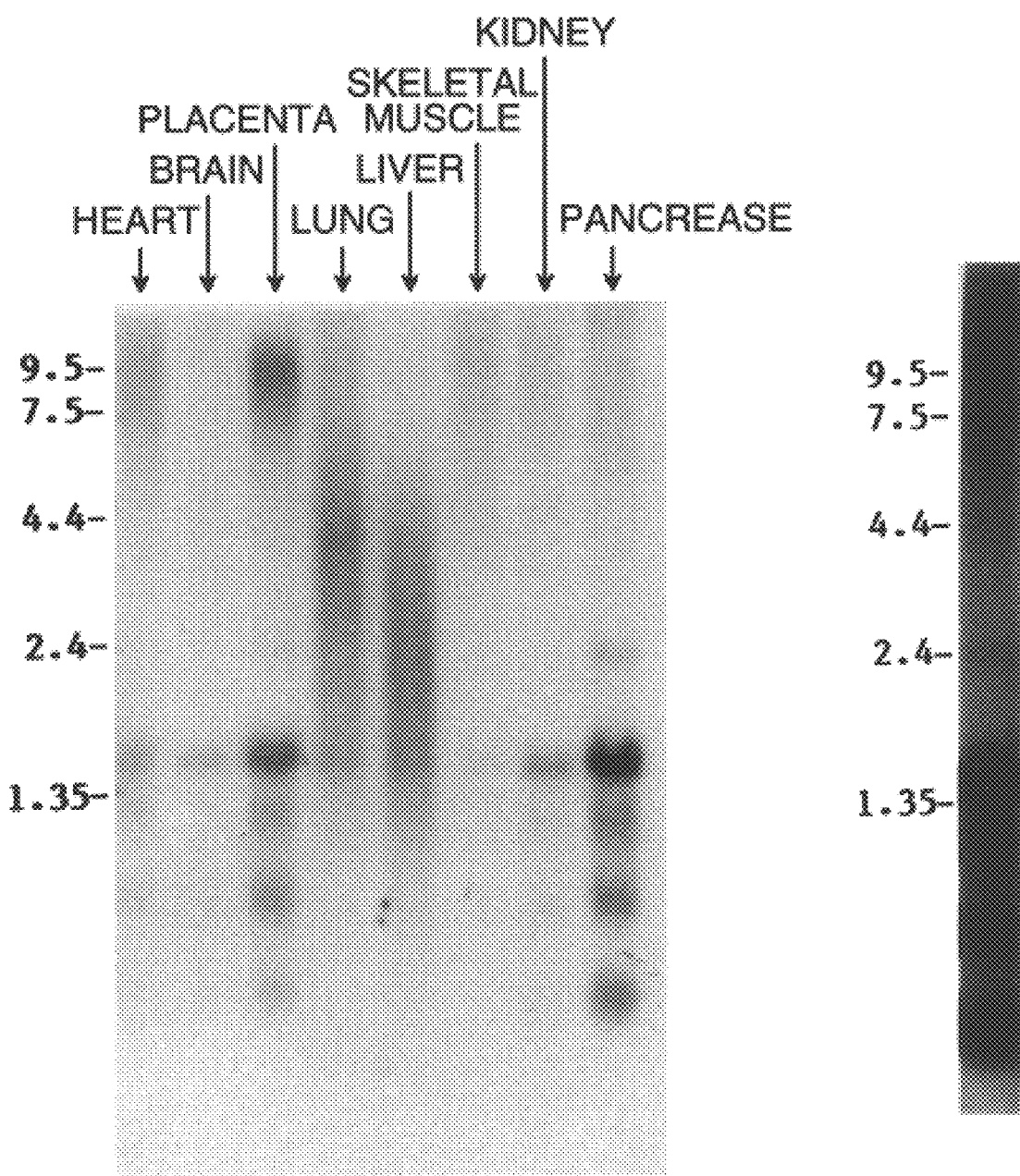
FIG. 6A and 6B show Northern blot analyses of N-SMase.

The 465 bp RT-PCR fragment amplified 5' end of N-SMase cDNA coding region was used to probe N-SMase mRNA in various human tissues. N-SMase was expressed in all the human tissues investigated, the transcript size and copy numbers varied from one tissue to another (see FIG. 6A of the drawings). The major transcript size of N-SMase expressed in all of these tissues is 1.7 kb. The other transcripts are 900 bp, 400 bp and 200 bp. Extended exposures of the x-ray film showed additional transcripts on the order of 2.5 kb and 4.0 kb (FIG. 6B) in human kidney. The cDNA of $\lambda^{32}$-1 consists of 3670 bp, and contains a polyadenylation signal (ATTATT) at 351, (ATTAAA) at 805, (AATTAA) at 2562 and (ATTAAA) at 2835. These polyadenylation signals vary from the consensus AATAAA sequence, but it was found in 12% (ATTAAA) and 2% (AATTAA, ATTATT) of the mRNAs in vertebrates, respectively. Such smaller transcripts exist due to their termination at different locations. The 1.7 kb transcript may be derived either from different genes or from alternative splicing.

Figure 7:
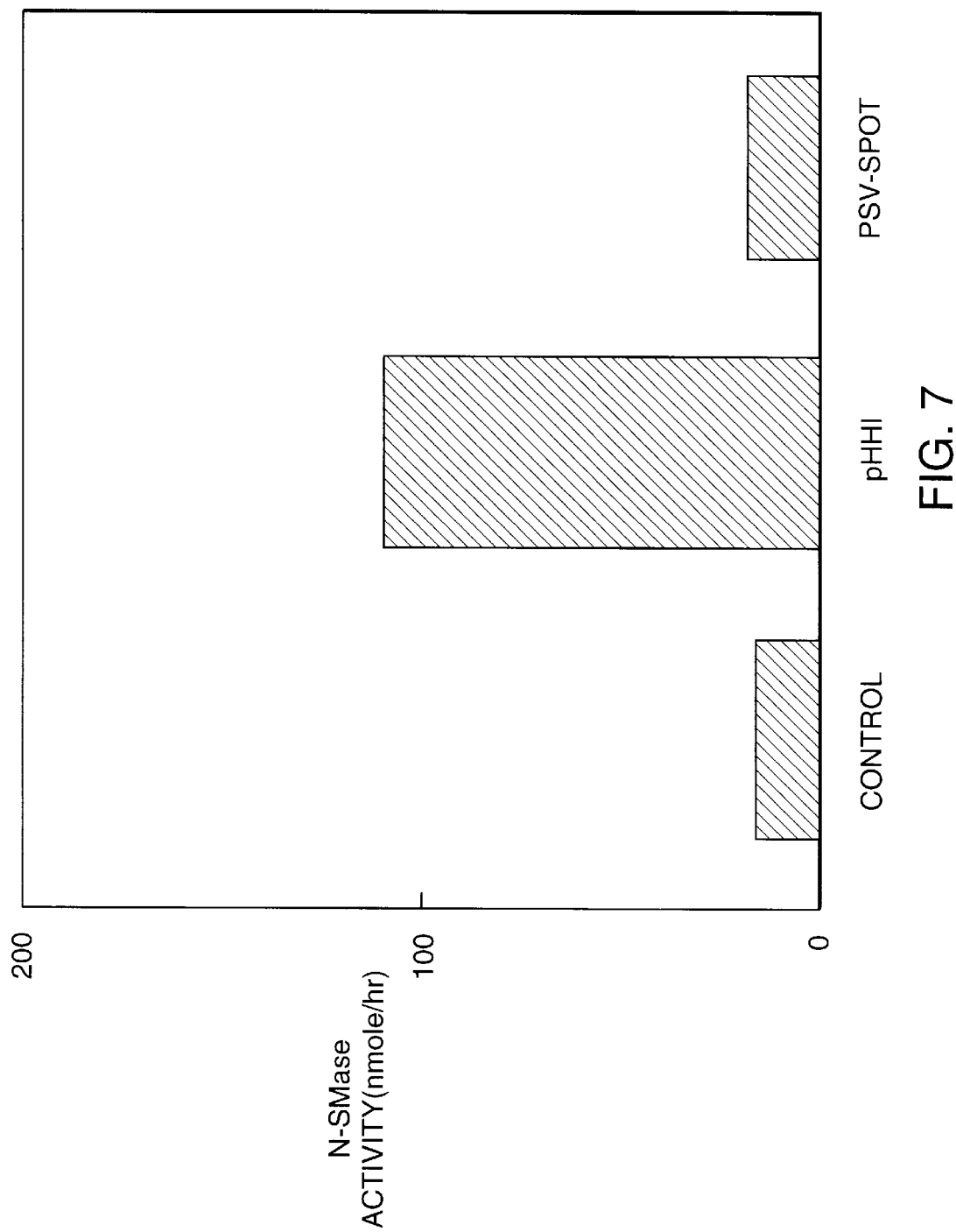
FIG. 7 shows N-SMase activity in aortic smooth muscle cells transiently transfected with cDNA for N-SMase.
Figure 8A:
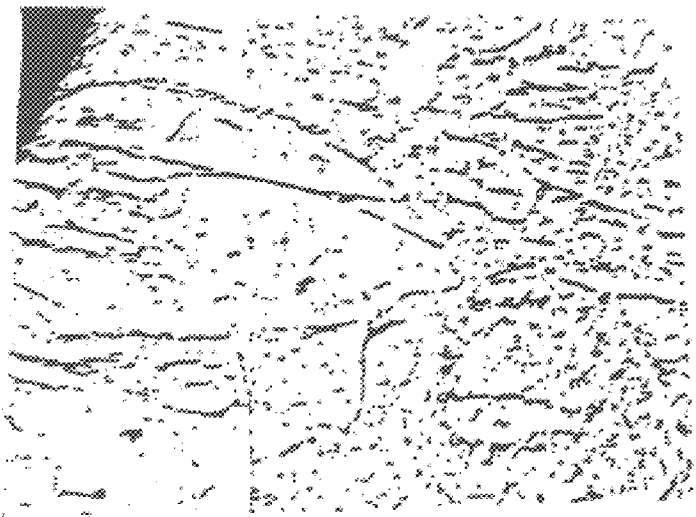
FIGS. 8A, 8B and 8C show chromatin condensation in transiently transfected aortic smooth muscle cells.
Figure 8B:
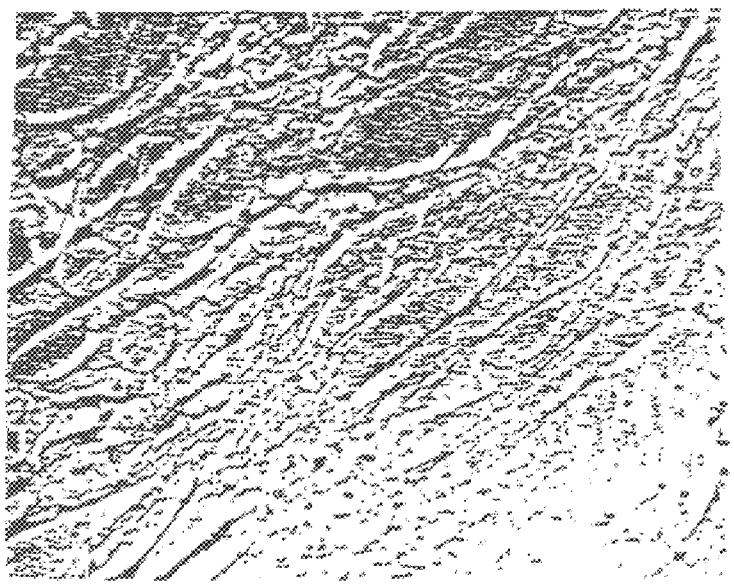
Figure 8C:
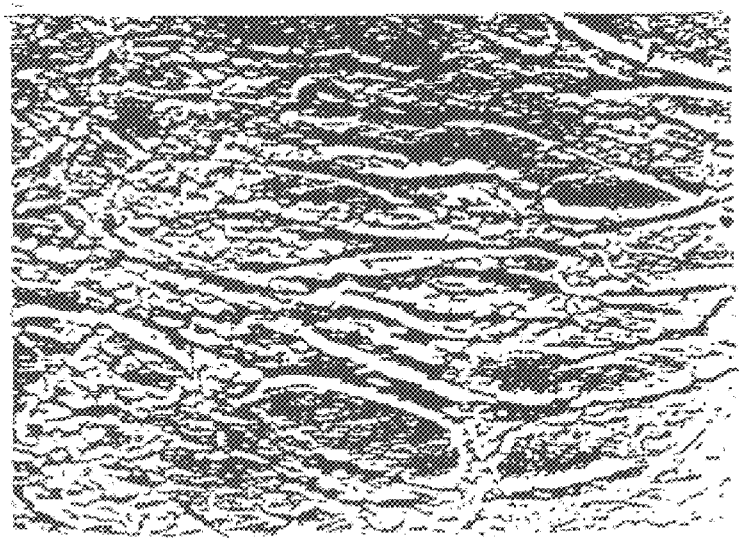

Aortic smooth muscle cells transiently transfected with pHH1 (cDNA for N-SMase) had a 5-fold increase in enzyme activity compared to control (pSVSPOT) (see FIG. 7). This was accompanied by DNA fragmentation in pHH1 transfected cells and chromatin condensation. Based on an analysis of about 500 cells, about 32% of the cells were found to be apoptotic (see FIG. 8C) as compared to control (FIG. 8A) and mock cDNA transfected cells (FIG. 8B). Those findings indicate that over-expression of N-SMase in aortic smooth muscle cells is accompanied by an increase in enzyme activity and apoptosis.

EXAMPLE 2

Protocol of a Preferred N-SMase Cleavage Assay.

A. Reagents: N-methyl-$^4$C]spingomyelin (22,000 dpm/2 µl in toluene:ethanol #:2 v/v). Cutsum (detergent) 0.002%, MgCl$_2$, 20 µg human serum albumin, 25 µMol Tris-glycine buffer pH 7.4. Enzyme (neutral sphingomyelinase) (1 ng–1 µg/well).

B. Preparation of Assay Plates:

First 2 µl of [$^{14}$C]sphingomyelin (22,000 dpm) is applied at the center of the PVDF well (Millipore MAIP-S-45-10), high protein binding Immobilon-P (0.4µ thick in a 96 well plastic tray. The assay plates are dried in vacuum and stored until use.

C. Assay:

The above reagents of Part A. are added to the well. Next, increasing concentration of the pure N-SMase (1 ng–1 µg) or samples of enzyme (human fluids, cell extracts, etc.) are added. Then, the sphingomyelinase assay (incubation at 37° C. for 30 minutes) is conducted. The contents of the reaction mixture are removed by suction attached to the bottom of the 96 well tray. After washing with PBS (5 times/50 µl) to remove non-specific radioactivity, 10 µl of liquid scintillation cocktail is added to each well and the [$^{14}$C] sphingomyelin radioactivity which remains on the PVDF 96 well tray is counted in a Packard top β counter.

This assay can be completely automated employing modern robotic systems. This assay also enables high-throughput, e.g. 96 samples can be conveniently assayed for sphingomyelinase in 30 minutes. The assay also enables screening or identifying both inhibitors (antagonists) and activators (agonists) of N-SMase. The assay also may be employed to assay any enzyme that requires a lipid as a substrate that can be adsorbed to PVDF. The method also may be employed for antigen antibody binding assays, receptors binding assays, bacterial assays, viral assays and other toxin binding assays.

D. Controls for Assays:

Purified N-Smase (1 ng–1 µg) is used as a standard control. Additionally, a constant set of samples (human urine) spiked with pure N-SMase are preferably employed and activity of such samples measured to serve as quality control and to assess day-to-day variation in the results.

The invention has been described in detail with reference to preferred embodiments thereof. However, it will be appreciated that those skilled in the art, upon consideration of this disclosure, may make modifications and improvements within the spirit and scope of the invention.

What is claimed is:

1. An isolated nucleic acid which codes for the human neutral sphingomyelinase represented by SEQ ID NO:2.

2. A recombinant vector comprising nucleic acid of claim 1.

3. A host cell comprising the vector of claim 2.

4. A method of producing human neutral sphingomyelinase comprising culturing a host cell of claim 3 under conditions suitable for expression of human neutral sphingomyelinase.

5. An isolated nucleic acid represented by the sequence of SEQ ID NO:1, or the complement thereto.

6. A recombinant vector comprising nucleic acid of claim 5.

7. A host cell comprising the vector of claim 6.

8. A method of producing human neutral sphingomyelinase comprising culturing a host cell of claim 7 under conditions suitable for expression of human neutral sphingomyelinase.

9. An isolated nucleic acid that hybridizes to the sequence of SEQ ID NO:1 using a hybridization buffer comprising 20% formamide in 0.8Msaline/0.08M sodium citrate (SSC) buffer at a temperature of 37° C. and remaining bound to washing once with that SSC buffer at 37° C., and that codes for a functional human neutral sphingomyelinase or fragment which fragment has human neutral sphingomyelinase activity.

10. The nucleic acid of claim 9 wherein the nucleic acid hybridizes to the sequence of SEQ ID NO:1 using a hybridization buffer comprising 20% formamide in 0.9Msaline/0.09M sodium citrate (SSC) buffer at a temperature of 42° C. and remaining bound to washing once with that SSC buffer at 42° C.

11. A recombinant vector comprising nucleic acid of claim 9.

12. A host cell comprising the vector of claim 11.

13. A fragment of SEQ ID NO:1 comprising at least about 20 base pairs and that codes for a polypeptide that has human neutral sphingomyelinase activity.

14. A fragment of SEQ ID NO:1 comprising at least about 100 base pairs and that codes for a polypeptide that has human neutral sphingomyelinase activity.

15. A fragment of SEQ ID NO:1 comprising at least about 300 base pairs and that codes for a polypeptide that has human neutral sphingomyelinase activity.

16. A fragment of SEQ ID NO:1 comprising at least about 500 base pairs and that codes for a polypeptide that has human neutral sphingomyelinase activity.

* * * * *